(12) United States Patent
Sasai

(10) Patent No.: US 8,866,109 B2
(45) Date of Patent: Oct. 21, 2014

(54) CHARGED-PARTICLE BEAM IRRADIATION DEVICE

(71) Applicant: Sumitomo Heavy Industries, Ltd., Tokyo (JP)

(72) Inventor: Kenzo Sasai, Niihama (JP)

(73) Assignee: Sumitomo Heavy Industries, Ltd., Tokyo (JP)

(*) Notice: Subject to any disclaimer, the term of this patent is extended or adjusted under 35 U.S.C. 154(b) by 0 days.

(21) Appl. No.: 14/068,190

(22) Filed: Oct. 31, 2013

(65) Prior Publication Data

US 2014/0058186 A1 Feb. 27, 2014

Related U.S. Application Data

(63) Continuation of application No. PCT/JP2012/060070, filed on Apr. 12, 2012.

(30) Foreign Application Priority Data

May 11, 2011 (JP) ................................. 2011-106562

(51) Int. Cl.
*G21K 5/04* (2006.01)
*A61N 5/10* (2006.01)
*G21K 1/093* (2006.01)

(52) U.S. Cl.
CPC ........ *A61N 5/1081* (2013.01); *A61N 2005/1087* (2013.01); *A61N 2005/1094* (2013.01); *A61N 5/1084* (2013.01); *G21K 1/093* (2013.01); *A61N 5/1042* (2013.01)
USPC ................. 250/492.3; 250/492.1; 250/396 R; 600/1; 315/500

(58) Field of Classification Search
USPC ............ 250/492.1, 396 R, 397, 492.3; 600/1; 315/500, 501, 502, 503, 504, 505, 506, 315/507
See application file for complete search history.

(56) References Cited

U.S. PATENT DOCUMENTS

| 5,039,057 A | 8/1991 | Prechter et al. |
| 2005/0063516 A1* | 3/2005 | Kato et al. ..................... 378/152 |
| 2011/0237859 A1* | 9/2011 | Kuhn et al. ....................... 600/1 |

FOREIGN PATENT DOCUMENTS

| JP | 06-060840 A | 3/1994 |
| JP | 08-201581 A | 8/1996 |

(Continued)

OTHER PUBLICATIONS

International Search Report dated May 15, 2012 corresponding to International Patent Application No. PCT/JP2012/060070.

(Continued)

*Primary Examiner* — Nicole Ippolito
(74) *Attorney, Agent, or Firm* — Squire Patton Boggs (US) LLP

(57) ABSTRACT

A charged-particle beam irradiation device, which irradiates an irradiation target with a charged-particle beam, includes a transport line that transports the charged-particle beam and a rotating gantry that is rotatable about a rotation axis. The transport line includes an inclination portion making the charged-particle beam travel so that the charged-particle beam is inclined to be separated from the rotation axis, and is formed to turn the charged-particle beam in a rotation direction of the rotation axis and to bend the charged-particle beam, which has turned in the rotation direction, toward the rotation axis. The rotating gantry is formed of a cylindrical portion that receives the irradiation target and supports the transport line. The inclination portion is disposed in the cylindrical portion of the rotating gantry. The charged-particle beam irradiation device further includes blocking members that block radiation emitted from the transport line disposed in the cylindrical portion.

4 Claims, 10 Drawing Sheets

(56) References Cited

FOREIGN PATENT DOCUMENTS

| | | | |
|---|---|---|---|
| JP | 2003-503120 A | 1/2003 | |
| JP | 2008-264311 A | 11/2008 | |
| JP | 2009-279045 A | 12/2009 | |
| WO | WO 2009/153864 A1 | 12/2009 | |

OTHER PUBLICATIONS

International Search Report international application No. PCT/JP2012/060070 dated Nov. 21, 2013.

* cited by examiner

CHARGED-PARTICLE BEAM IRRADIATION DEVICE

BACKGROUND

1. Technical Field

The present invention relates to a charged-particle beam irradiation device that performs the irradiation of a charged-particle beam.

2. Description of the Related Art

A device, which performs cancer treatment by irradiating a patient with a charged-particle beam such as a proton beam, is known. This kind of device includes a cyclotron (accelerator) that emits a charged-particle beam by accelerating charged particles, a rotating gantry (rotating body) on which a rotatable irradiation unit irradiating a patient with the charged-particle beam in an arbitrary direction is mounted, and a transport line that transports the charged-particle beam emitted from the cyclotron to the irradiation unit.

The irradiation unit is rotatable relative to the patient, and various forms are known as the form of the transport line that transports a charged-particle beam to the irradiation unit. For example, the beam transport line mounted on the rotating gantry disclosed in the related art is disposed to make the charged-particle beam, which travels in a direction of the rotation axis of the rotating gantry, travel so that the charged-particle beam is inclined to be separated from the rotation axis, to make the charged-particle beam travel by a predetermined distance after turning the charged-particle beam in a rotation direction of the rotation axis, and to transport the charged-particle beam to the irradiation unit (nozzle 32) by bending the charged-particle beam, which has traveled by the predetermined distance, toward the rotation axis. Further, the beam transport line, which is disposed as described above, is supported by a truss-like structure (rotating gantry).

SUMMARY

According to an embodiment of the present invention, there is provided a charged-particle beam irradiation device that irradiates an irradiation target with a charged-particle beam. The charged-particle beam irradiation device includes a transport line that transports the charged-particle beam and a rotating gantry that is rotatable about a rotation axis. The transport line includes an inclination portion making the charged-particle beam, which travels in a direction of the rotation axis, travel so that the charged-particle beam is inclined to be separated from the rotation axis, and is formed to turn the charged-particle beam, which has traveled through the inclination portion, in a rotation direction of the rotation axis and to bend the charged-particle beam, which has turned in the rotation direction, toward the rotation axis. The rotating gantry is formed of a cylindrical portion that receives the irradiation target and supports the transport line. The inclination portion of the transport line is disposed in the cylindrical portion of the rotating gantry. The charged-particle beam irradiation device further includes blocking members that block radiation emitted from the transport line disposed in the cylindrical portion.

DETAILED DESCRIPTION

Figure 1:
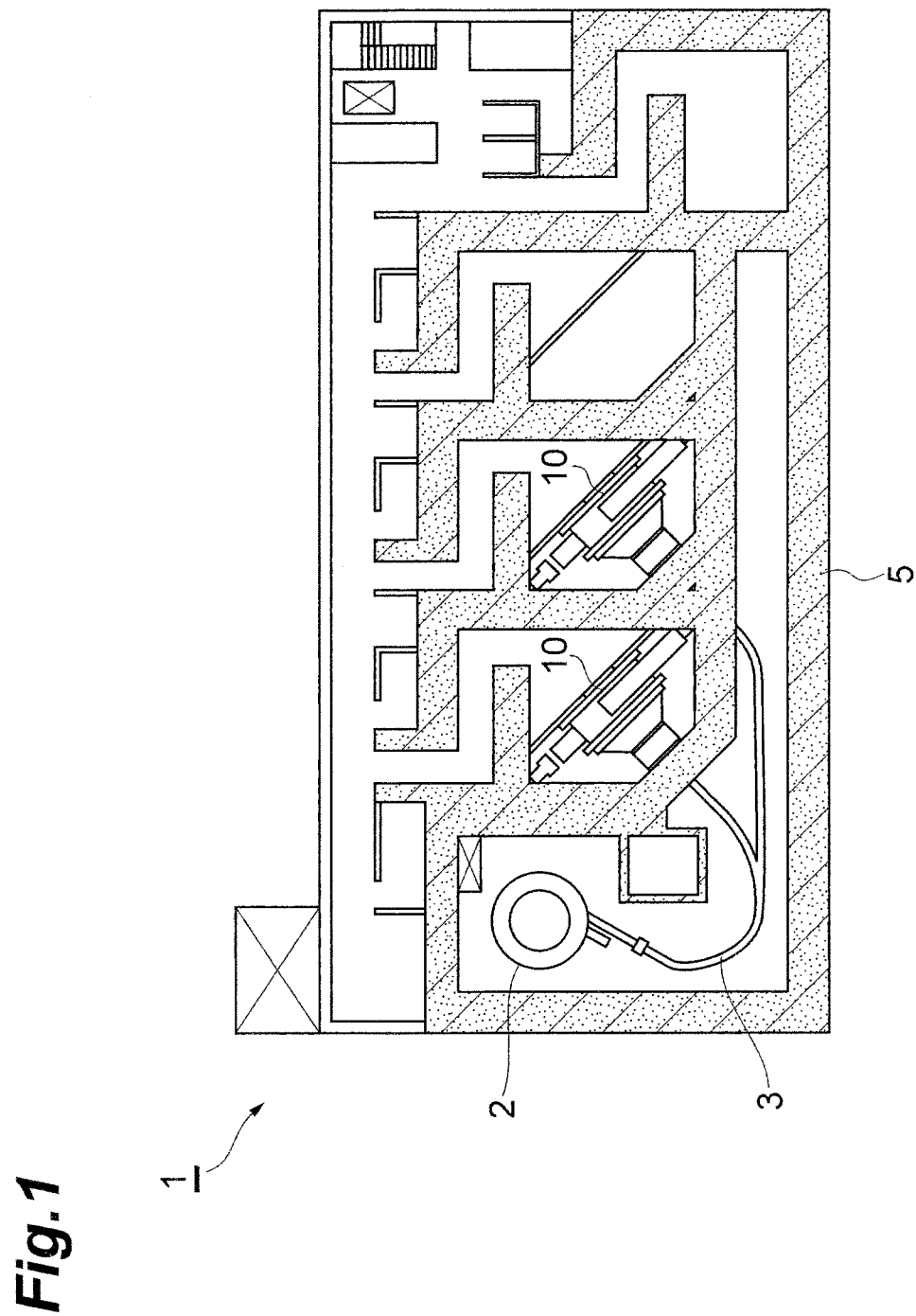
FIG. 1 is a schematic view showing the structure of a proton therapy system including a proton therapy device according to an embodiment of the invention.

However, the length of the beam transport line disclosed in the related art in the direction of the rotation axis is reduced, so that the device is miniaturized. However, the size of the device in the radial direction, which is a direction crossing the rotation axis, is very large. Further, since electromagnets and the like of the beam transport line are supported by the truss-like structure that is formed so as to protrude outward in the radial direction, the size of the entire rotating gantry in the radial direction is very large. For this reason, the size of a space in which the rotating gantry is received is also increased, which causes the increase of the size of a building in which the rotating gantry is installed. Accordingly, it is difficult to reduce construction costs.

Furthermore, when the beam transport line is disposed close to an irradiation target for the miniaturization of the charged-particle beam irradiation device, it is required to reduce radiation that is emitted to the irradiation target from the beam transport line.

It is desirable to miniaturize a charged-particle beam irradiation device and to reduce radiation that travels toward the side where an irradiation target is present.

The charged-particle beam irradiation device according to the embodiment of the invention includes the rotating gantry that includes a cylindrical portion rotatable about the rotation axis, and a part of the transport line that transports the charged-particle beam is formed so as to pass through the cylindrical portion of the rotating gantry. As a part of the transport line, the inclination portion, which makes the charged-particle beam, which travels in a direction of the rotation axis, travel so that the charged-particle beam is inclined to be separated from the rotation axis, is disposed so as to pass through the cylindrical portion. When the inclination portion of the transport line, which is separated from the rotation axis in the radial direction, is disposed so as to pass through the cylindrical portion of the rotating gantry as described above, it is possible to reduce the protruding length of the transport line in the radial direction and to reduce the size of the entire device in the radial direction as compared to when the transport line is disposed so as to avoid a cylindrical portion (for example, enclosure or an irradiation chamber). Accordingly, it is possible to reduce a space in which the charged-particle beam irradiation device is received and to miniaturize a building. Since it is possible to reduce the amount of concrete, which is used to form, for example, the radiation blocking walls of the building by miniaturizing the building, it is possible to reduce the construction costs of the building.

Further, since the blocking members that block radiation emitted from the transport line disposed in the cylindrical portion are provided, it is possible to block the radiation, which is emitted from the transport line, by the blocking members. Accordingly, it is possible to suppress entry of the radiation emitted from the transport line to the irradiation chamber (enclosure).

Further, the transport line disposed in the cylindrical portion may make the charged-particle beam pass therethrough and include electromagnets that adjust the charged-particle beam, the electromagnet may include a plurality of yokes that protrude inward, and each of the blocking members may be disposed between the adjacent yokes. When the blocking members are disposed between the yokes as described above, it is possible to fill the gaps between the yokes, through which radiation may pass, with the blocking members. Accordingly, it is possible to reduce radiation that is emitted to the outside of the electromagnets.

Furthermore, the charged-particle beam irradiation device may further include the blocking members that are installed on the outer surfaces of electromagnets. According to this structure, it is possible to block radiation by the blocking members that are installed on the outer surfaces of the electromagnets. Accordingly, it is possible to prevent the radiation from entering a treatment room.

Moreover, the charged-particle beam irradiation device may further include a plurality of blocking members that are made of different materials. When the charged-particle beam irradiation device further includes a plurality of blocking members that are made of different materials as described above, it is possible to dispose the plurality of blocking members according to the energy level of radiation. Accordingly, it is possible to suitably block radiation.

According to the embodiment of the invention, it is possible to miniaturize the charged-particle beam irradiation device, to reduce a space in which the device is received, and to miniaturize a building. Accordingly, it is effective in reducing the construction costs of the building in which the charged-particle beam irradiation device is installed. Further, according to the embodiment of the invention, it is possible to suppress entry of radiation emitted from the electromagnets to an irradiation chamber in which an irradiation target is present.

A charged-particle beam irradiation device according to a preferred embodiment of the invention will be described below with reference to the drawings. In this embodiment, a proton therapy system including a proton therapy device (charged-particle beam irradiation device) will be described. The proton therapy device is applied to, for example, cancer treatment, and is a device that irradiates a tumor (irradiation target) in the body of a patient with a proton beam (charged-particle beam).

As shown in FIG. 1, a proton therapy system 1 includes a cyclotron (particle accelerator) 2 that emits a proton beam by accelerating ions generated from an ion source (not shown), a beam transport line 3 that transports the proton beam emitted from the cyclotron 2, and a proton therapy device 10 that irradiates an irradiation target with the proton beam transported by the beam transport line 3. Further, the respective devices of the proton therapy system 1 are received in a building 5.

The proton beam accelerated by the cyclotron 2 is deflected along the beam transport line 3 and is supplied to the proton therapy device 10. The beam transport line 3 is provided with deflection magnets that deflect a proton beam, quadrupole electromagnets that form a beam, or the like. Quadrupole electromagnets that form a beam, deflection magnets that deflect a beam, and the like are included in electromagnets that adjust a charged-particle beam.

As shown in FIGS. 2 to 8, the proton therapy device 10 includes a beam introduction line (transport line) 31 to which a proton beam is introduced by the beam transport line 3 and which transports the proton beam, a beam irradiation nozzle 11 that irradiates an irradiation target with the proton beam transported by the beam introduction line 31, and a rotating gantry 12 that supports the beam introduction line 31 and the beam irradiation nozzle 11 and is rotatable about a predetermined rotation axis P.

Figure 4:
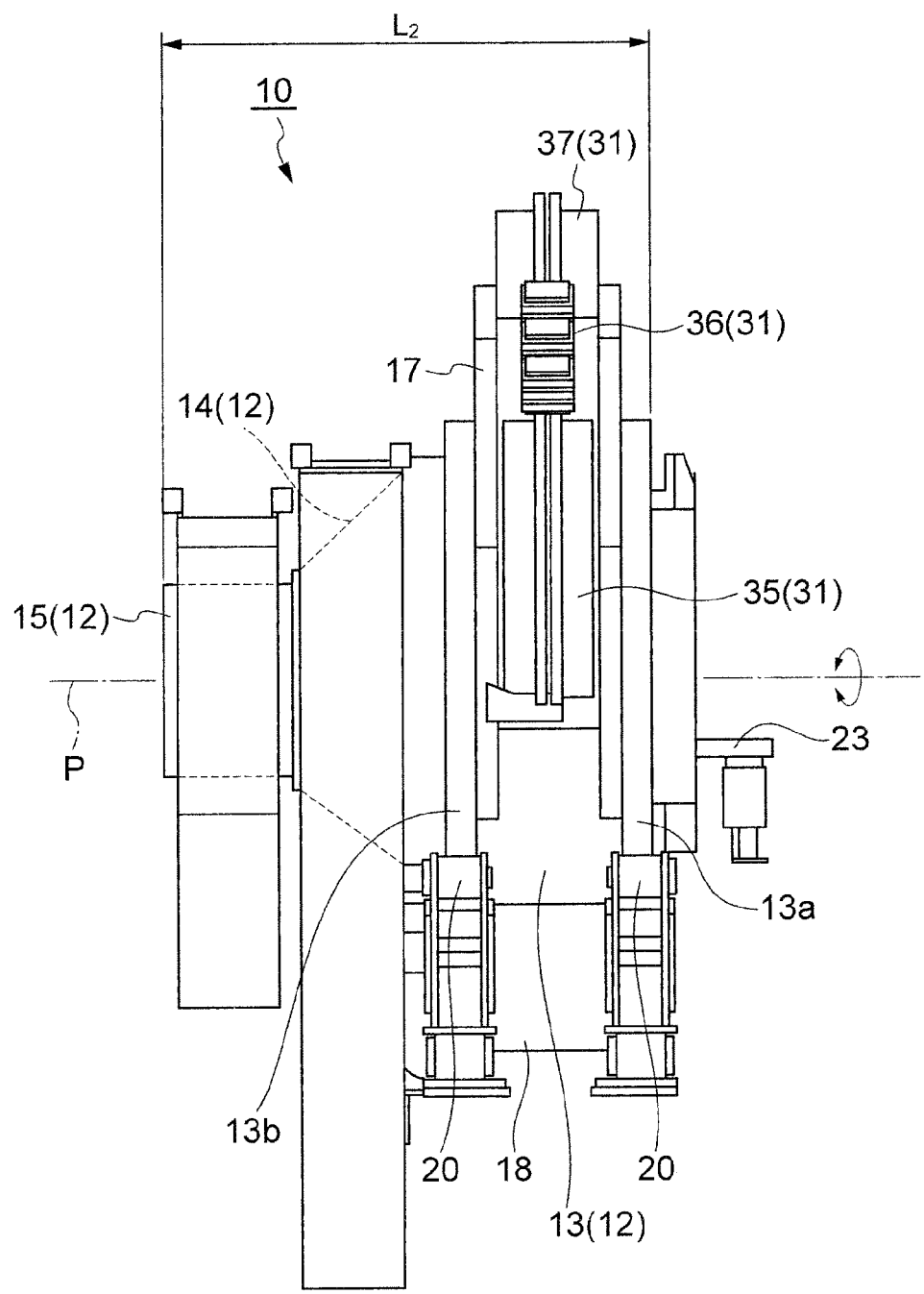
FIG. 4 is a right side view of the proton therapy device according to the embodiment of the invention.
Figure 5:
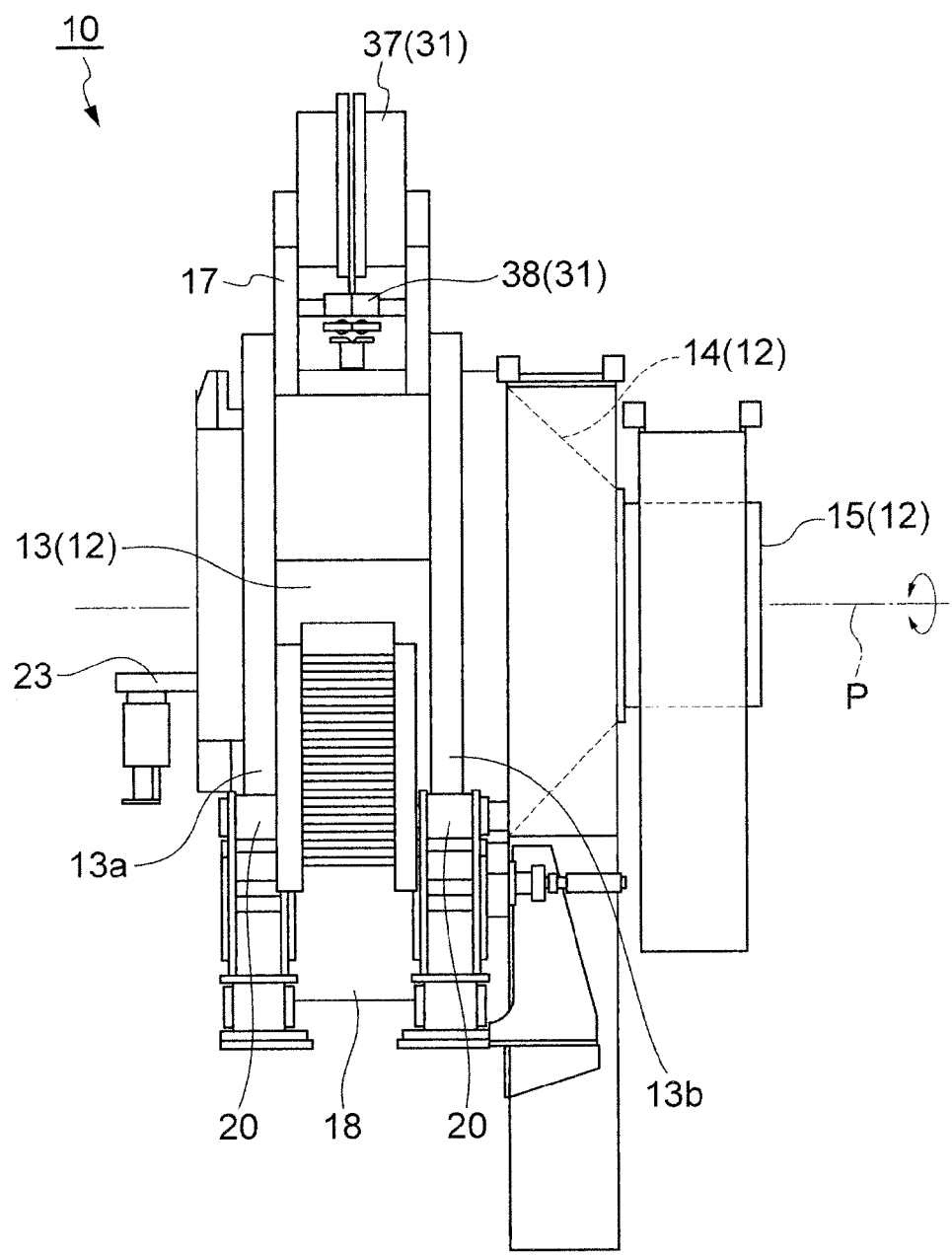
FIG. 5 is a left side view of the proton therapy device according to the embodiment of the invention.
Figure 6:
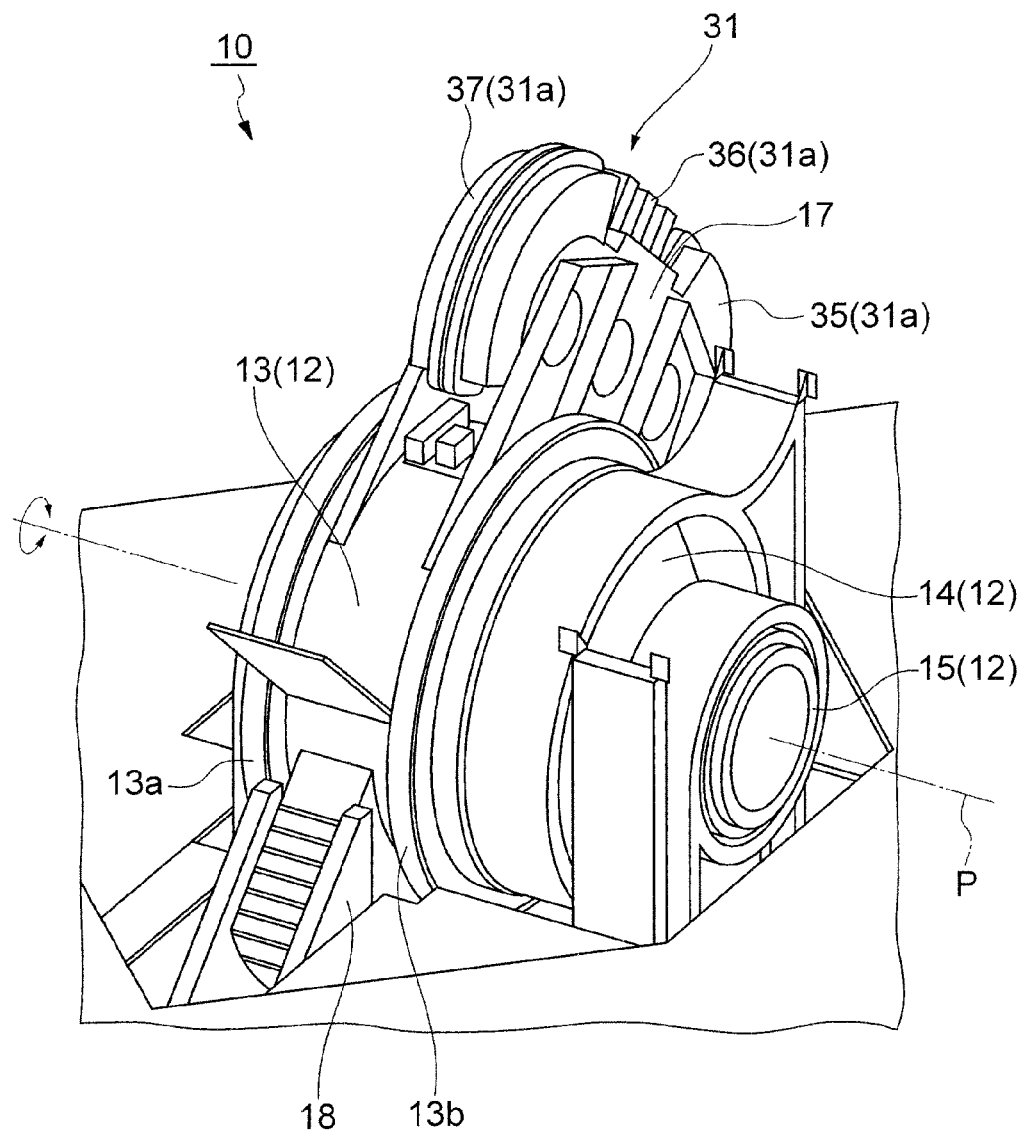
FIG. 6 is a perspective view of the proton therapy device according to the embodiment of the invention when seen obliquely from the rear side.

As shown in FIGS. 4 to 6, the rotating gantry 12 includes a cylindrical body portion 13, a cone portion 14, and a second cylindrical portion 15 that are disposed in this order in the direction of the rotation axis P. The cylindrical body portion 13, the cone portion 14, and the second cylindrical portion 15 are disposed on the same axis (rotation axis P) and are connected to each other.

Meanwhile, the side on which the cylindrical body portion 13 is disposed is referred to as the front side of the rotating gantry 12 and the side on which the second cylindrical portion 15 is disposed is referred to as the rear side of the rotating gantry 12.

The cylindrical body portion 13 and the second cylindrical portion 15 are cylindrical bodies having a thin-wall structure, and are formed to be capable of reducing weight while maintaining stiffness. The diameter of the second cylindrical portion 15 is smaller than the diameter of the cylindrical body portion 13, and the cone portion 14 is formed in a conical shape so as to be connected to the cylindrical body portion 13 and the second cylindrical portion 15. The cone portion 14 is a cylindrical portion having a thin-wall structure, and is formed so that the inner diameter of the cone portion is reduced from the front side to the rear side. Further, the length of the rotating gantry 12 in the direction of the rotation axis P (a distance between the front end portion of the cylindrical body portion 13 and the rear end portion of the second cylindrical portion 15), that is, $L_2$ is set to about 4.6 m.

Ring parts 13a and 13b having, for example, a rectangular cross-sectional shape are provided at both end portions of the cylindrical body portion 13 in the direction of the rotation axis P. As shown in FIGS. 2 to 5, the cylindrical body portion 13 is rotatably supported by a roller unit 20 that is disposed below the cylindrical body portion 13. The roller unit 20 functions as a drive unit that rotates the rotating gantry 12.

The front side of the cylindrical body portion 13 is opened, so that radiation can enter the cylindrical body portion 13. Meanwhile, a rear panel (partition wall) 16 is provided on the rear side of the cylindrical body portion 13. Further, an irradiation chamber 21 is formed by the cylindrical body portion 13 and the rear panel 16. A bed (treatment table) 22 on which a patient, that is, an irradiation target lies can be disposed in the irradiation chamber 21. The bed 22 can be moved by a robotic arm 23. The bed 22 is disposed outside the rotating gantry 12 (irradiation chamber 21) in a normal time when treatment is not performed. The bed 22 is disposed in the irradiation chamber 21 when treatment is performed. Meanwhile, the bed 22 is not shown in FIG. 7.

The beam irradiation nozzle 11 is fixed to the inner surface of the cylindrical body portion 13, and is rotated about the rotation axis P together with the cylindrical body portion 13. The beam irradiation nozzle 11 is moved with the rotation of the cylindrical body portion 13, so that the emission direction of a proton beam is changed.

The beam introduction line 31, which is a beam transport line of the proton therapy device 10, is connected to the beam transport line 3 that transports the proton beam emitted from the cyclotron 2. The beam introduction line 31 introduces the proton beam, which is transported by the beam transport line 3, into the beam irradiation nozzle 11.

Figure 8:
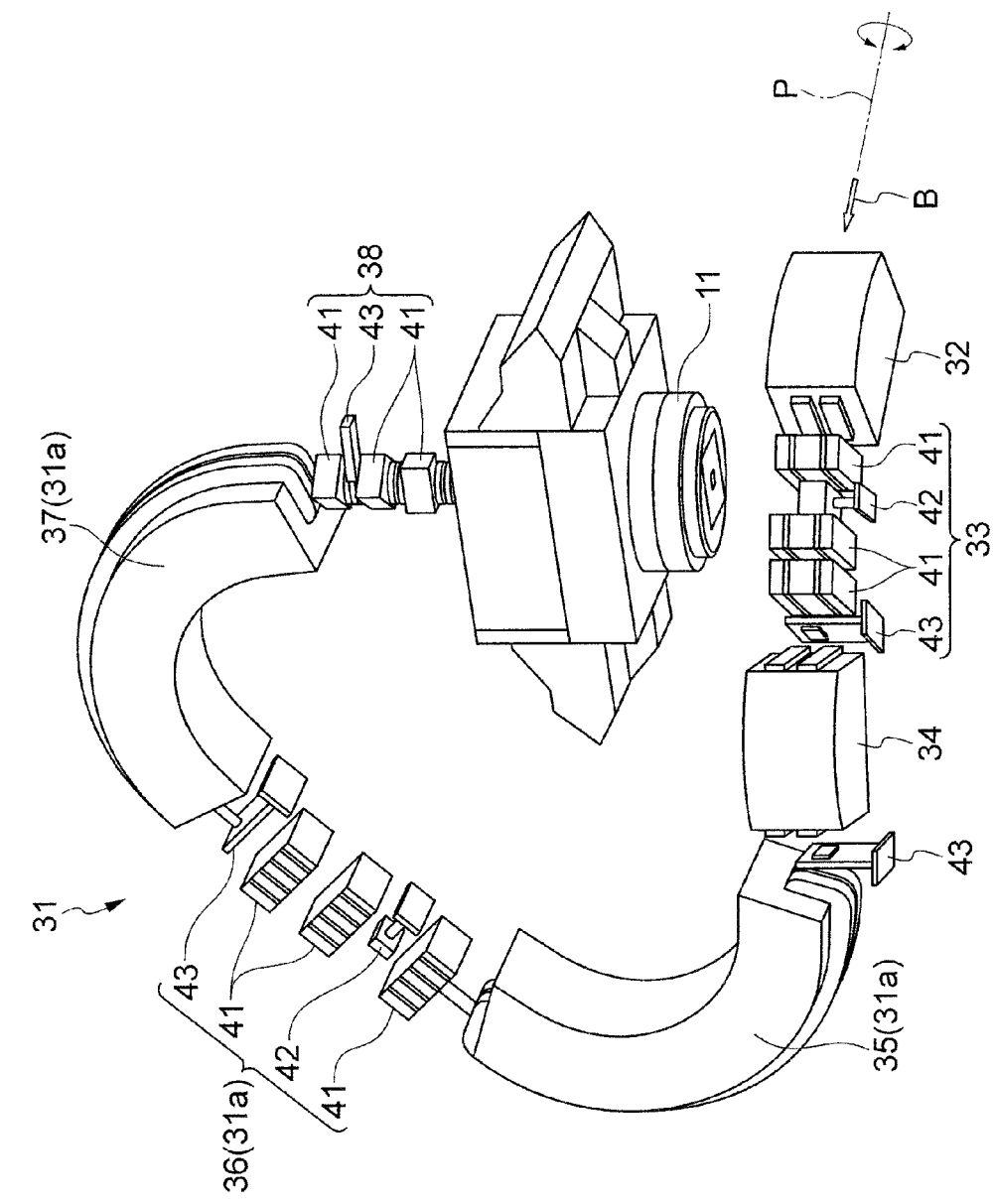
FIG. 8 is a perspective view showing a beam introduction line and a beam irradiation nozzle mounted on the rotating gantry.

FIG. 8 is a perspective view showing the beam introduction line 31 and the beam irradiation nozzle 11 mounted on the rotating gantry 12. The beam introduction line 31 includes a first bend portion 32 that deflects a proton beam B traveling in the direction of the rotation axis P of the rotating gantry 12, an inclination portion 33 that is provided downstream of the first bend portion 32 and makes the proton beam B travel in a direction inclined with respect to the direction of the rotation axis P, a second bend portion 34 that is provided downstream of the inclination portion 33 and deflects the proton beam B in a direction orthogonal to the rotation axis P, a third bend portion 35 that is provided downstream of the second bend portion 34 and turns the proton beam B in the rotation direction of the rotation axis P, a linear portion 36 that is provided downstream of the third bend portion 35 and makes the proton beam B travel to the upper side of the beam irradiation nozzle 11 (the upper side in FIG. 2), a fourth bend portion 37 that is provided downstream of the linear portion 36 and bends the proton beam B toward an axis (the rotation axis P), and a linear portion 38 that is provided downstream of the fourth bend portion 37 and makes the proton beam B travel toward the beam irradiation nozzle 11.

The proton beam B travels through a vacuum duct 47 (see FIG. 9) that is provided in the beam introduction line 31. The respective electromagnets provided in the beam introduction line 31 are provided so as to surround the vacuum duct 47. The beam introduction line 31 may not be provided with the linear portion 36. When the beam introduction line 31 is not provided with the linear portion 36, the fourth bend portion 37 is provided downstream of the third bend portion 35. In this case, the third bend portion 35 and the fourth bend portion 37 may be integrated with each other.

The first bend portion 32 is formed of a 45-degree deflection electromagnet that bends the proton beam B to deflect the proton beam B by an angle of 45°. The inclination portion 33 includes optical elements, such as quadrupole electromagnets 41, a steering electromagnet 42, and a profile monitor 43. The quadrupole electromagnets 41 have a function of adjusting the size or the optical focus position of the proton beam B at an irradiation position. The steering electromagnet 42 has a function of moving a beam axis in parallel. The profile monitor 43 has a function of detecting the shape and position of the proton beam B that passes therethrough. Each of the inclination portion 33 and the linear portion 36 may not include one of the quadrupole electromagnets 41, the steering electromagnet 42, and the profile monitor 43.

The second bend portion 34 is formed of a 45-degree deflection electromagnet that bends the proton beam B to deflect the proton beam B by an angle of 45°. Further, a profile monitor 43 is disposed between the second bend portion 34 and the third bend portion 35. The third bend portion 35 is formed of a 135-degree deflection electromagnet that bends the proton beam B to deflect the proton beam B by an angle of 135°. The profile monitor 43, which is disposed between the second bend portion 34 and the third bend portion 35, may be omitted.

The linear portion 36 includes quadrupole electromagnets 41, a steering electromagnet 42, and a profile monitor 43. The fourth bend portion 37 is formed of a 135-degree deflection electromagnet that bends the proton beam B to deflect the proton beam B by an angle of 135°. The linear portion 38 includes quadrupole electromagnets 41 and a profile monitor 43.

Figure 7:
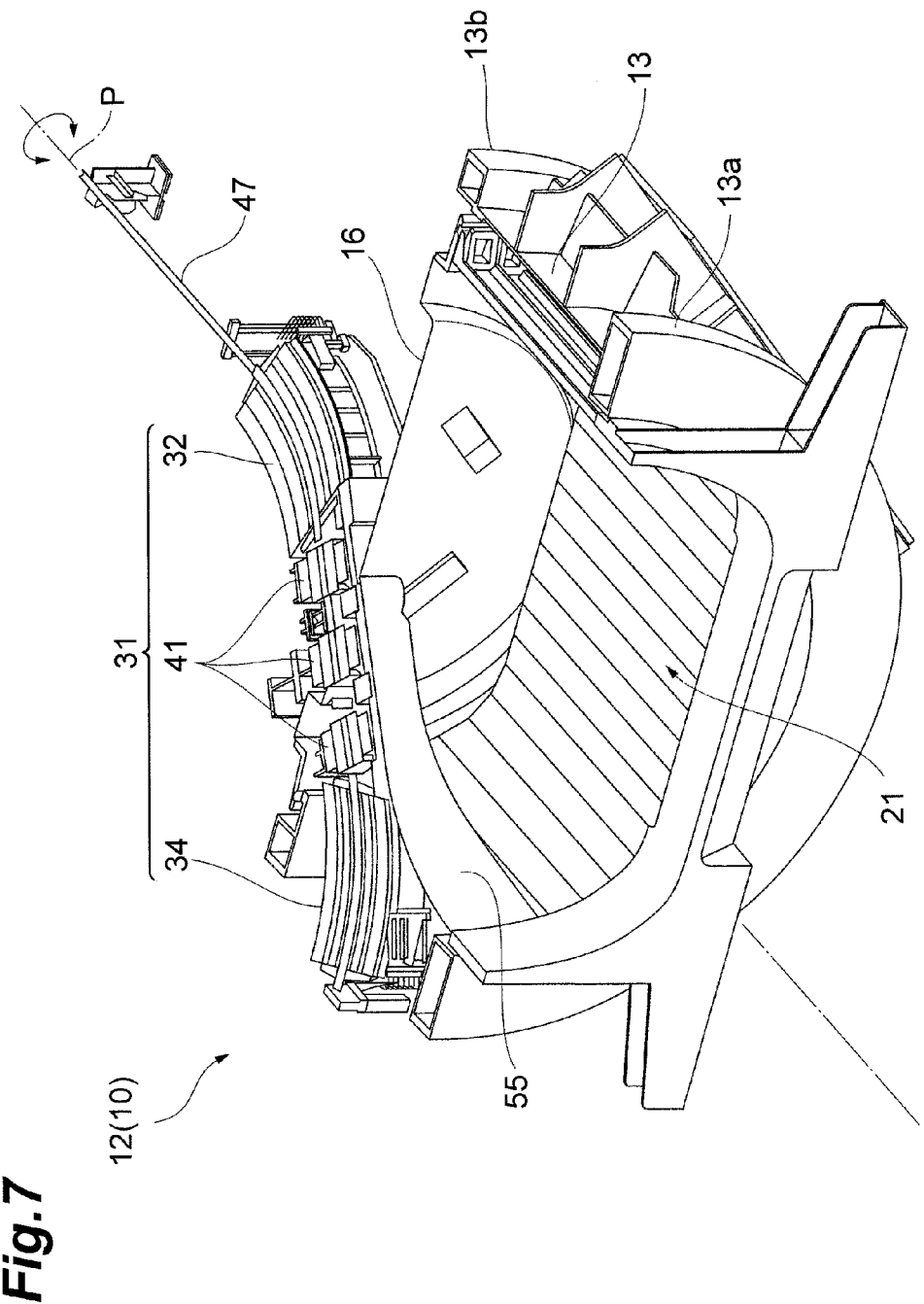
FIG. 7 is a cross-sectional perspective view of a rotating gantry of the proton therapy device according to the embodiment of the invention.

Here, as shown in FIG. 7, in the proton therapy device 10 according to this embodiment, a part of the beam introduction line 31 mounted on the rotating gantry 12 is disposed so as to pass through the cylindrical portions (the cylindrical body portion 13, the cone portion 14, and the second cylindrical portion 15) of the rotating gantry 12. The proton beam B, which is transported by the beam transport line 3, is introduced inward from the rear side of the second cylindrical portion 15; passes through the second cylindrical portion 15, the cone portion 14, the rear panel 16, and the cylindrical body portion 13; and is led to the outside of the cylindrical body portion 13 through the cylindrical body portion 13.

Figure 9:
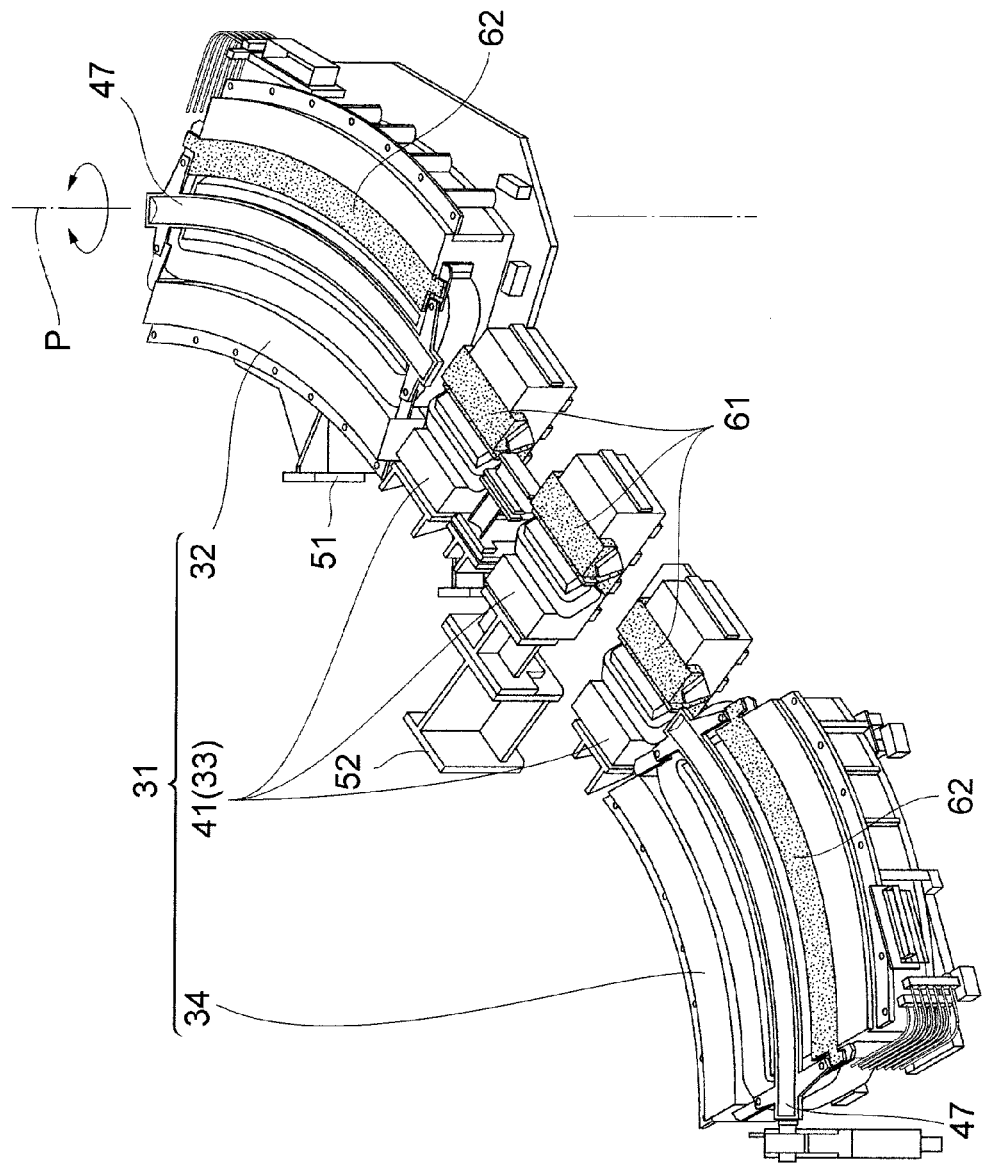
FIG. 9 is a cross-sectional view of the beam introduction line that is disposed in the rotating gantry.

As shown in FIG. 9, the rotating gantry 12 includes first and second support members 51 and 52 that support the beam introduction line 31. The first bend portion 32 is fixed to the second cylindrical portion 15 by the first support member 51. The inclination portion 33 is fixed to the cone portion 14 by the second support member 52, passes through the rear panel 16, and is supported by the rear panel 16. The second bend portion 34 passes through the cylindrical body portion 13 and is supported by the cylindrical body portion 13.

As shown in FIG. 7, the beam introduction line 31 enters the cylindrical body portion 13 through the rear panel 16 and is disposed so as to pass through the irradiation chamber 21. Further, the rotating gantry 12 includes a casing 55 that receives the beam introduction line 31 passing therethrough. The casing 55 is disposed along the beam introduction line 31 and covers the beam introduction line 31. One end portion of the casing 55 is supported by the rear panel 16 and the other end portion thereof is formed so as to continue to the side wall of the cylindrical body portion 13.

Figure 2:
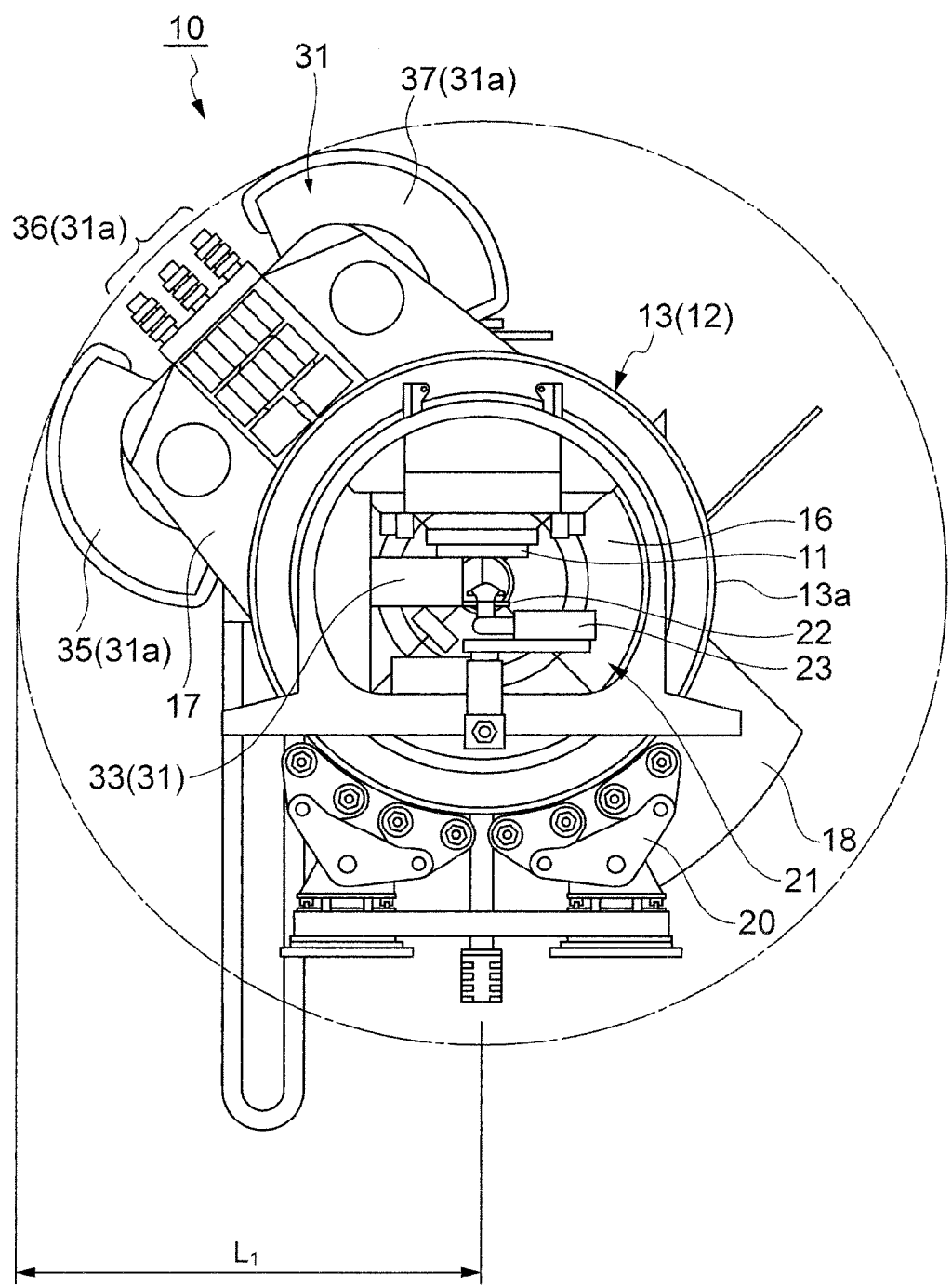
FIG. 2 is a front view of the proton therapy device according to the embodiment of the invention.
Figure 3:
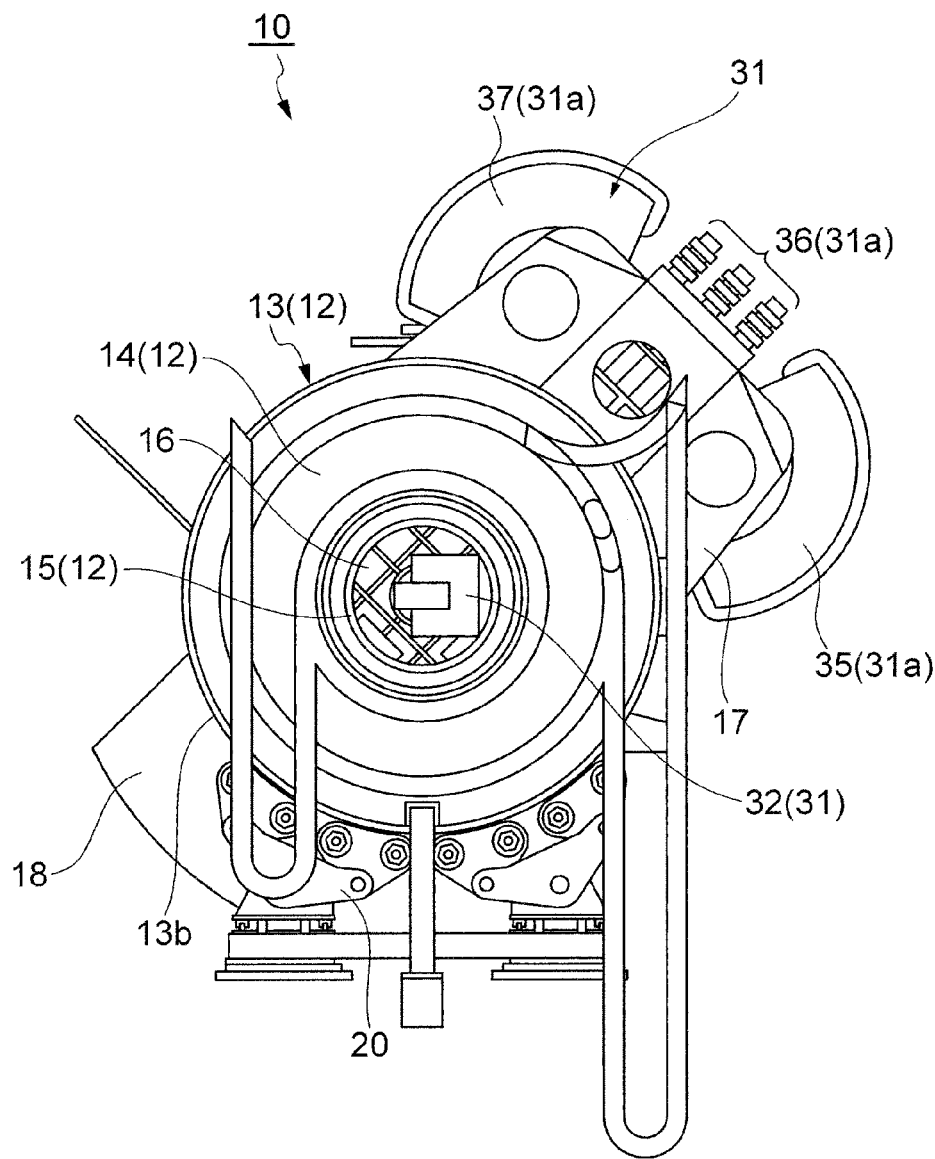
FIG. 3 is a rear view of the proton therapy device according to the embodiment of the invention.

Furthermore, as shown in FIG. 2, a frame 17, which supports the beam introduction line 31 protruding outward from the cylindrical body portion 13, is provided on the outer peripheral surface of the cylindrical body portion 13. Meanwhile, the beam introduction line 31 protruding outward from the cylindrical body portion 13 is referred to as a beam introduction line-protruding portion 31a. The third bend portion 35, the linear portion 36, and the fourth bend portion 37 are included in the beam introduction line-protruding portion 31a. The frame 17 is fixed to the outer surface of the cylindrical body portion 13 and protrudes outward in the radial direction. The frame 17 supports the beam introduction line-protruding portion 31a from the inside in the radial direction. Accordingly, the load of the electromagnets (the quadrupole electromagnets 41 and the 135-degree deflection electromagnets) and the like can be received by the cylindrical body portion 13.

Moreover, a counter weight 18 is provided on the outer peripheral surface of the cylindrical body portion 13 so as to face with the rotation axis P interposed therebetween. Since the counter weight 18 is installed, the weight balance against the third bend portion 35, the linear portion 36, the fourth bend portion 37, and the frame 17, which are disposed on the outer surface of the cylindrical body portion 13 is ensured.

Further, rollers of the roller unit 20 are rotated by a motor (not shown), so that the rotating gantry 12 is rotationally driven. The rotation of the rotating gantry 12 is stopped by a brake unit (not shown).

Figure 10:
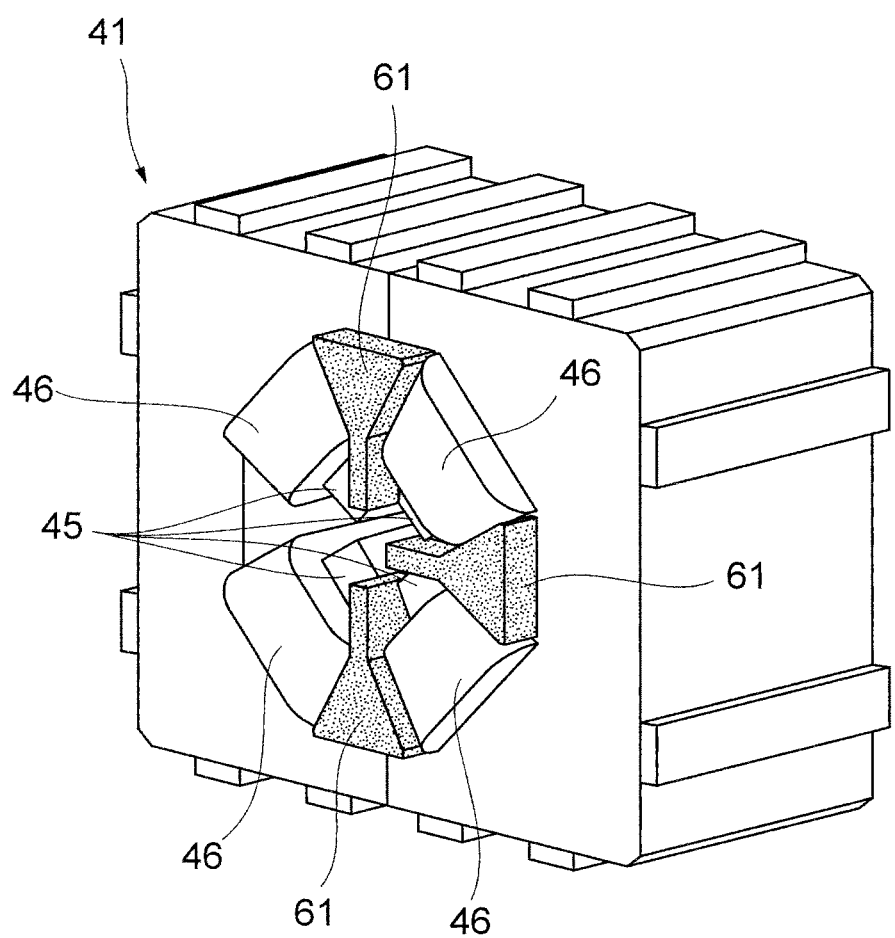
FIG. 10 is a perspective view of a quadrupole electromagnet of the beam introduction line.

Here, as shown in FIGS. 7, 9, and 10, the rotating gantry 12 of the proton therapy system 1 includes blocking members 61 and 62 that block radiation from the beam introduction line 31 disposed in the cylindrical body portion 13. Each of the blocking members 61 and 62 is made of a material that blocks radiation, such as gamma rays or neutron rays. Examples of the material of the blocking members 61 and 62 include iron, polyethylene, boron-added polyethylene, stainless steel, concrete, and the like. In this embodiment, stainless steel is employed as the material of the blocking members 61 and 62.

The blocking members 61 are disposed in the spaces formed in the quadrupole electromagnets 41 and the blocking members 62 are disposed in the spaces formed in the 45-degree deflection electromagnets (the first and second bend portions 32 and 34). FIG. 10 is a perspective view of the quadrupole electromagnet. As shown in FIG. 10, an opening is formed at the center of the quadrupole electromagnet 41 and the vacuum duct 47 (see FIG. 7) through which a charged-particle beam passes is inserted into the opening. The quadrupole electromagnet 41 includes a plurality of (four) yokes 45 that protrude inward and coils 46 that are wound around the yokes 45. Meanwhile, the vacuum duct 47 is not shown in FIG. 10. The vacuum duct 47 is disposed along the beam introduction line 31 and forms a vacuum space through which a proton beam passes.

Further, each of the blocking members 61 is disposed between the yokes 45 that are adjacent to each other in a predetermined circumferential direction centered on the vacuum duct 47. Specifically, each of the blocking members 61 is disposed so as to fill the space between the coils 46 that are wound around the yokes 45. The blocking members 61 are disposed along the longitudinal direction of the vacuum duct 47. The blocking members 61 are supported by coming into contact with, for example, the adjacent coils 46.

Furthermore, each of the blocking members 62, which are disposed in the 45-degree deflection electromagnets 32 and 34, is disposed so as to fill the space between the adjacent yokes (between the coils), like the blocking members 61 that are disposed in the quadrupole electromagnets 41. The blocking members 61 and 62 of this embodiment are disposed in the spaces corresponding to sides of arrows A, B, and C (an irradiation target and the rotation axis P) of FIG. 9 among the spaces between the yokes 45, and are not disposed on the side of an arrow D (on the side opposite to the irradiation target). The blocking members 61 and 62 may be disposed in all of the spaces between the yokes 45, and may be disposed in only a part of the spaces.

In this proton therapy system 1, the proton beam B emitted from the cyclotron 2 is transported by the beam transport line 3 and reaches the proton therapy device 10. The proton beam B having reached the proton therapy device 10 is transported by the beam introduction line 31, reaches the beam irradiation nozzle 11, and irradiates the tumor of a patient. The irradiation direction of the proton beam B, which is irradiated from the beam irradiation nozzle 11, can be adjusted by the rotation of the rotating gantry 12.

In this proton therapy device 10, a part of the beam introduction line 31, which transports the proton beam B, is formed so as to pass through the second cylindrical portion 15, the cone portion 14, and the cylindrical body portion 13 of the rotating gantry 12. Particularly, the inclination portion 33 of the beam introduction line 31 is obliquely disposed so as to pass through the irradiation chamber 21 (the cylindrical body portion 13) and can lead the beam introduction line 31, which is introduced from the rear side of the rotating gantry 12, from the side of the rotating gantry 12. For this reason, it is possible to reduce the protruding length of the beam introduction line 31 (a distance $L_1$ between the rotation axis P and the maximum outer diameter) as compared to when the beam transport line is formed so as to avoid the irradiation chamber 21. Accordingly, it is possible to miniaturize the proton therapy device 10, and to miniaturize an installation space in which the proton therapy device 10 is installed. As a result, it is possible to miniaturize the building 5 that receives the proton therapy device 10. Since it is possible to reduce the amount of concrete, which is used to form, for example, the radiation blocking walls of the building by miniaturizing the building, it is possible to reduce the construction costs of the building. Meanwhile, as shown in FIG. 2, the maximum rotational outer diameter of the proton therapy device 10 can be set to 10.6 m ($L_1 \times 2$).

Further, in the proton therapy device 10, a part (the inclination portion) of the beam introduction line 31 is obliquely disposed so as to pass through the rear panel 16 and the irradiation chamber 21. Accordingly, it is possible to reduce the length of the beam introduction line 31, which is disposed on the rear side of the irradiation chamber 21, as compared to when the beam introduction line 31 is formed so as to avoid the irradiation chamber 21. That is, the entire proton therapy device 10 is miniaturized even in the direction of the rotation axis P.

Furthermore, in the proton therapy device 10 according to this embodiment, the beam introduction line (beam transport line) 31 is supported by the cylindrical body portion (cylindrical portion) 13 of the rotating gantry 12. Accordingly, since the plurality of electromagnets, which are optical elements of the beam introduction line 31, are supported by the cylindrical body portion 13 functioning as a strengthening member and the weight of the electromagnets can be received by the cylindrical body portion 13, it is possible to suitably disperse a force that is applied to the cylindrical body portion 13. Moreover, since the rear panel 16 is provided at one end portion of the cylindrical body portion 13, it is possible to make the rear panel 16 function as a strengthening member.

Further, in the proton therapy device 10 according to this embodiment, the blocking members 61 and 62 are installed in the electromagnets (the quadrupole electromagnets 41 and the deflection magnets 32 and 34) of the beam introduction line 31 that is disposed in the cylindrical body portion 13 of the rotating gantry 12. It is possible to suppress entry of the radiation emitted from the beam introduction line 31 to the irradiation chamber 21, by the blocking members 61 and 62.

The proton beam, which travels through the vacuum duct 47 of the beam introduction line 31, bumps against the vacuum duct 47, so that gamma rays or neutron rays are emitted. Since the blocking members 61 and 62, which block the radiation generated from the vacuum duct 47 provided in the electromagnets 41, 32, and 34, are provided in this embodiment, it is possible to suppress entry of the radiation generated from the vacuum duct 47 to the irradiation chamber 21 and to reduce concern about the exposure of a patient to the radiation. Accordingly, the beam introduction line 31 can be disposed close to the bed 22, so that it is possible to miniaturize the rotating gantry 12.

Furthermore, since the blocking members 61 and 62 are disposed in the spaces between the yokes 45 provided in the electromagnets 41, 32, and 34, it is possible to effectively use the spaces between the yokes 45 and to suppress the emission of the radiation to the irradiation chamber 21 from the vacuum duct 47.

The invention has been specifically described above on the basis of the embodiment thereof, but the invention is not limited to the above-mentioned embodiment. For example, the disposition or the number of the respective elements, such as the electromagnets 41, of the beam introduction line 31 may be appropriately changed according to a predetermined beam design.

Further, the particle accelerator is not limited to the cyclotron and may be a synchrotron or a synchrocyclotron. Furthermore, a charged-particle beam is not limited to a proton beam, and may be a carbon beam (heavy particle beam) or the like. Moreover, the cylindrical portion of the rotating gantry 12 is not limited to a cylinder and may be other cylindrical bodies. Further, the cylindrical portion of the rotating gantry 12 has the same shape in the direction of the rotation axis P.

The rotating gantry 12 does not need to be rotated (oscillated) by an angle of 360°, and may be rotated (oscillated) by an angle smaller than 360°.

Furthermore, a notch may be formed at a part of the cylindrical portion, for example, the side wall. Meanwhile, a structure in which the beam introduction line 31 is disposed so as to pass through the cylindrical portion also includes a structure in which the beam introduction line 31 is disposed in the notch formed at the cylindrical portion.

Moreover, the notch may be formed at the rear panel. Meanwhile, a structure in which the beam introduction line 31 is disposed so as to pass through the rear panel also includes a structure in which the beam introduction line 31 is disposed in the notch formed at the rear panel. The beam introduction line 31 may be disposed so as to pass through a notch or an opening formed at the rear panel.

Further, the inclination portion has been formed in a linear shape in the above-mentioned embodiment, but may be an inclination portion that is gently curved.

Furthermore, the blocking members may be installed on the outer surfaces of the electromagnets. For example, the blocking members may be provided on both gaps formed in the electromagnets and the outer surfaces of the electromagnets, and may be disposed only on the outer surfaces of the electromagnets or only in the gaps formed in the electromagnets.

Moreover, the blocking member is disposed in the gap between the outer surface of the electromagnet and the casing 55 (see FIG. 7). Further, the casing 55 itself may function as a blocking member.

Furthermore, when a plurality of blocking members are provided, different materials may be employed according to the disposition of the blocking members. For example, stainless steel may be employed for the blocking member disposed in the electromagnet, and polyethylene may be employed for the blocking member disposed on the outer surface of the electromagnet. If stainless steel is employed for a portion which is close to the vacuum duct and at which the energy of radiation is high and polyethylene is employed for a portion which is distant from the vacuum duct and at which the energy of radiation is low as described above, it is possible to effectively block radiation. The materials of the blocking members may be changed according to an energy level. Moreover, the blocking member 61 of the quadrupole electromagnet 41 and the blocking members 62 of the deflection electromagnets 32 and 34 may be made of different materials.

Further, the blocking members may be disposed not only on the beam introduction line 31 that is disposed in the cylindrical portion but also on a portion of the beam introduction line 31 that is adjacent to the cylindrical portion. For example, the blocking members may be provided in the electromagnets of the beam introduction line 31 that is disposed on the rear side of the rear panel 16.

Furthermore, if a nonmagnetic material is employed as the material of the blocking members 61 and 62 disposed in the electromagnets 41, 32, and 34, it is possible to prevent an adverse influence on a magnetic field.

According to the charged-particle beam irradiation device of an embodiment of the invention, it is possible to miniaturize the device, to reduce a space in which the device is received, and to miniaturize a building. Accordingly, it is possible to reduce the construction costs of the building in which the charged-particle beam irradiation device is installed. Further, according to an embodiment of the invention, it is possible to suppress entry of radiation emitted from the electromagnets to an irradiation chamber in which an irradiation target is present.

It should be understood that the invention is not limited to the above-described embodiment, but may be modified into various forms on the basis of the spirit of the invention. Additionally, the modifications are included in the scope of the invention.

What is claimed is:

1. A charged-particle beam irradiation device that irradiates an irradiation target with a charged-particle beam, the charged-particle beam irradiation device comprising:
   a transport line configured to transport the charged-particle beam; and
   a rotating gantry that is rotatable about a rotation axis, and
   a beam irradiating nozzle configured to irradiate the irradiation target with the charged-particle beam transported by the transport line,
   wherein the transport line includes an inclination portion configured to make the charged-particle beam, which travels in a direction of the rotation axis, travel so that the charged-particle beam is inclined to be separated from the rotation axis, a turning portion to turn the charged-particle beam, which has traveled through the inclination portion, in a rotation direction of the rotation axis, and a bending portion to bend the charged-particle beam, which has turned in the rotation direction, toward the rotation axis,
   the rotating gantry is formed of a cylindrical portion configured to receive the irradiation target and supports the transport line, and
   the inclination portion of the transport line is disposed in the cylindrical portion of the rotating gantry,
   the charged-particle beam irradiation device further comprising:
   blocking members configured to block secondary radiation emitted from the inclination portion of the transport line disposed in the cylindrical portion by the transport line transporting the charged-particle beam.

2. The charged-particle beam irradiation device according to claim 1,
   wherein the transport line disposed in the cylindrical portion makes the charged-particle beam pass therethrough and includes electromagnets configured to adjust the charged-particle beam,
   the electromagnet includes a plurality of yokes configured to protrude inward, and
   each of the blocking members is disposed between the adjacent yokes.

3. The charged-particle beam irradiation device according to claim 1, further comprising:
   the blocking members that are installed on the outer surfaces of electromagnets.

4. The charged-particle beam irradiation device according to claim 1, further comprising:
   a plurality of the blocking members that are made of different materials.

* * * * *